United States Patent [19]
Hiruma et al.

[11] Patent Number: 5,914,107
[45] Date of Patent: Jun. 22, 1999

[54] METHOD OF INTRODUCING AN ENDOPHYTIC FUNGUS INTO ROUGH BLUEGRASS BELONGING TO *POA TRIVIALIS* AND *POA COMPRESSA*

[75] Inventors: Naoya Hiruma; Satoshi Shinozaki, both of Fujinomiya, Japan

[73] Assignee: Mayekawa Manufacturing Co., Ltd., Tokyo, Japan

[21] Appl. No.: 08/933,755

[22] Filed: Sep. 23, 1997

[30] Foreign Application Priority Data

Sep. 27, 1996  [JP]  Japan .................................... 8-277110

[51] Int. Cl.$^6$ .............................. A01N 63/00; C12N 1/14; C12N 5/00
[52] U.S. Cl. ...................... 424/93.5; 435/254.1; 435/410
[58] Field of Search ........................ 424/93.5; 435/254.1, 435/410

[56] References Cited

FOREIGN PATENT DOCUMENTS

| | | |
|---|---|---|
| 73853 91 | 10/1991 | Australia . |
| 0 753 259 | 1/1997 | European Pat. Off. . |
| 409051734 | 2/1997 | Japan . |
| 7-51734 | 2/1997 | Japan . |

OTHER PUBLICATIONS

Latch et al., "Artificial infection of grasses with endophytes", Ann.Appl.Biol. 1985, 107, pp. 17–24.

Bacon C W: "Isolation, Culture, and Maintenance of Endophytic Fungi of Grasses", 1990, Isolation of Biotechnological Organisms from Nature, pp. 259–282, XP000651392.

Database WPI, Section Ch, Week 9550, Derwent Publications Ltd., London, GB; class C05, AN 95–390189, XP 002052385.

Database WPI, Section Ch, Week 9551, Derwent Publications Ltd., London, GB; Class C06, An 95–3991881, XP002052386.

Reed, C. et al.; Biotecnology of Endophytic Fungui of grasses:, CRC Press, Inc. XP002026706.

Johnson M C et al: "Infection of Tall Fescue with *Acremonium coenophialum* by Means of Callus Culture" Plant Disease, vol. 70, No. 5, May 1, 1986, pp. 380–382, XP00577476.

White J F et al: "Endophyte–Host Associations in Forage Grasses x. Cultural Studies on Some Species of Acremonium Sect Albo–Lanosa, including a New Species, a Starril", Mycotaxon, vol. 30, Oct. 1987, pp. 87–95, XP000602391.

O'Sullivan B D et al: "Infection of Plantlets, Derived from Pyegrass and Tall Fescue Meristems, with Acremonium Endophytes" Proceedings of the International Symposium on Acremonium/Grass Interactions, Jan. 1, 1993, p. 16/17 XP00578512.

*Primary Examiner*—Sandra E. Saucier
*Assistant Examiner*—Vera Afremova
*Attorney, Agent, or Firm*—Kanesaka & Takeuchi

[57] ABSTRACT

To provide rough bluegrasses having improved characteristics, and in particular improved insect resistance and disease resistance, an endophyte comprising a filamentous endophytic fungus living in wild plants that exist in nature is isolated and artificially grown, and rough bluegrasses are then inoculated and infected with the artificially grown endophyte so that the endophyte lives symbiotically in the rough bluegrasses. In particular, rough bluegrasses *Poa trivialis* and *Poa compressa* and endophytic fungus Acremonium sp. Po-060 (FERM P-15862).

15 Claims, No Drawings

METHOD OF INTRODUCING AN ENDOPHYTIC FUNGUS INTO ROUGH BLUEGRASS BELONGING TO *POA TRIVIALIS* AND *POA COMPRESSA*

BACKGROUND OF THE INVENTION

1. Field of the Invention

This invention is related to method of introducing an endophytic fungus into rough bluegrass. Herein, rough bluegrass refers to a plant which is a Pooideae belonging to the genus Poa which is a part of Poeae and includes *Poa trivialis* and *Poa compressa*.

2. Description of Related Art

Bluegrasses known in the art include Kentucky bluegrass, Canada bluegrass, annual bluegrass, rough meadowgrass, bulbous meadowgrass, alpine meadowgrass, wavy meadowgrass, wood meadowgrass, Balfour's meadowgrass, swamp meadowgrass, broad-leaved meadowgrass, narrow-leaved meadowgrass, smooth meadowgrass, spreading meadowgrass and flattened meadowgrass.

Of these, rough bluegrass is known by its English name of rough meadowgrass (Japanese name oosuzumenokatabira).

These plants are members of the group Pooideae, and also belong to the genus Poa which is a part of Poeae. For example, rough bluegrass is known as *Poa trivialis*. *Poa trivialis* is a plant classified by Clayton et al (Genera Graminium, Grasses of the World, 1986).

Of the many bluegrasses, rough bluegrasses are of particular importance to man, and are widely used in meadow and pasture.

Rough bluegrasses have a wide utility, and as they cover very large areas, they are subjected to damage from disease or pests. Damage due to bluegrass webworm (Japanese name Shibata moth) is severe, and in areas where pesticide sprays have not reached, grass can disappear overnight as soon as the larvae have hatched.

Conventional methods of cultivating and growing grasses include the artificial crossing method, selection method, mutation method, cell fusion method and gene insertion method. Due to recent progress in biotechnology, the cultivation period which previously required 10 years or more, has been reduced to several years. As regards genetic insertion which is a character transformation tequnigue, several techniques exist such as a method using agrobacterium, the electroporation method and the particle gun method, and they are now being applied to a large variety of crops.

However, in the case of grasses which comprise staple crops, it has been pointed out that this genetic insertion is extremely inefficient. In the case of the agrobacterium method it is difficult to infect grasses, so genetic insertion is very difficult. As regards the electroporation method, a regeneration system has to be developed from the protoplast of the grass, and even if such a regeneration is possible, the characteristics of the plant may suffer damage due to culture mutations.

Concerning the particle gun method, since genes are randomly introduced into the plant organism or culture, the plant obtained frequently becomes a chimera.

In the case of grasses including rough bluegrass, cell culture techniques such as cell fusion or genetic insertion require complex operating procedures and as they are not very efficient, there are very few examples where they have successfully been applied at a practical level.

However, there are some wild plants in nature in which filamentous fungi which are internal fungi, i.e. endophytes, live together with the plant. They grow particularly well in the gaps between cells, i.e. the intercellular spaces.

These endophytes, or symbiotic filamentous fungi, not only have no adverse effect on the host plant but in fact provide it with useful substances, and contribute to help withstanding environmental stresses.

Enhancement by endophytes of plant properties is known from the literature, e.g. insect resistance (Siegel et al, 1987, Ann. Rev. Phytopathol. 25: 293–315), disease resistance (Gwinn and Gavin, 1992, Plant Disease 76: 911–914), environmental stress (drought, etc.) resistance (Arachevalta et al, 1989, Agron J. 81: 83–90), and growth enhancement (Latch et al, 1985, N.Z.J. Agric. Res. 28: 165–168). It is particularly well-known that, in perennial rye grass infected with endophytes, these endophytes improve insect resistance due to the repelling substances and alkaloids they produce.

Latch et al in New Zealand are searching for endophytes known as endosafes which have low toxicity to livestock and excellent insect resistance by collecting and studying endophytes in perennial rye grass.

As many of the plants in which these endophytes live have little utility, it is necessary to introduce them into useful grasses. In this regard, attempts have already been made to introduce endophytes into perennial rye grass which is an important pasture grass. The techniques used may be broadly distinguished as artificial crossing and artificial inoculation.

In artificial crossing, useful characteristics are introduced by pollen using a plant infected by an endophyte as mother, but using the conventional method, there were limitations on the species and strains which could be crossed with one another. On the other hand, in artificial inoculation, plants or culture tissues are inoculated with endophytes that have been separated and cultivated.

The artificial inoculation method is capable of introducing a wider range of types, however due to problems of technique regarding cultivation of endophytes, inoculation conditions and conditions of the plant itself, it is limited to perennial rye grass. To increase the infection rate, a method has been reported where callus is used as the plant tissue which is inoculated. However according to this method, it is necessary to develop a plant regeneration system from the callus, hence the method was still limited to perennial rye grass.

The conventional cell cultivation method involves a troublesome procedure and requires considerable training. It was moreover difficult in practical application since culture mutations caused by character transformation or cell fusion had an effect on the characteristic being introduced or on other characteristics.

In the genetic insertion method, it was not possible to introduce specific characteristics if it was not known which genes had an effect on the characteristics and type of a plant.

Characteristics related to complex factors such as environmental stress could not be introduced by techniques such as genetic insertion. Moreover, plants grown by cell culture techniques were often found to exhibit decreased seed fertility. In the case of grasses this led to a decline of yield and was therefore fatal.

In view of the above, growth techniques using endophytes or improvement of characteristics are a totally new approach to solving the above problems.

When endophytes are introduced into plants by artificial inoculation, due to problems in searching for endophytes and cultivation systems, the technique is limited to perennial rye grass and has never been applied to other useful grasses, such as rough bluegrass. In callus inoculation, it is essential to develop a regenerating system of the plant into which the endophyte is to be introduced. Moreover, inoculation conditions had not been developed to increase the rate of infection of the endophyte.

At present, useful endophytes have been found only in perennial rye grass, tall fescue and meadow fescue which constitute a major limitation to their introduction. In particular, these host plants are foreign types, and no endophytes derived from Japanese original plants had yet been found that were adapted to Japanese environmental conditions.

OBJECTS AND SUMMARY OF THE INVENTION

It is therefore an object of this invention to provide a method of artificially introducing such an endophyte into rough bluegrasses i.e. *Poa trivialis* and *Poa compressa*, which are originally uninfected by endophytes.

A further object this invention is to provide a rough bluegrasses, at least insect resistance and disease resistance may be conferred on which by artificially introducing an endophyte such that the endophyte lives in the rough bluegrass in a symbiotic relationship.

A still further object of this invention is to provide a rough bluegrasses, the characteristics of which are improved, and useful rough bluegrasses having excellent characteristics.

One aspect of this invention relates to bluegrasses obtained by artificially introducing an endophytic filamentous fungus, i.e. an endophyte, into rough bluegrasses not originally infected with an endophyte. In the context of this invention, the term rough bluegrass refers to a member of the grass family, and to a plant which belongs to the genus Poa under Poaea which is a part of Pooideae. This plant is known by the English name of rough meadowgrass (Japanese name oosuzumenokatabira).

Herein, the term rough bluegrass includes plants having the academic name *Poa trivialis* and *Poa compressa*. It also includes strains such as Sabre, Darkhorse and Colt which are sold commercially.

To introduce the endophyte into these rough bluegrasses, a search is made to discover endophytes living in plants growing in nature. An endophyte is isolated from the plants, and an artificial culture of it is made which is then introduced. Plants occurring in nature on which endophytes are known to live include Cyperaceae and Juncaceae.

The following endophyte was found and cultivated by the inventors, and may be used for the present purpose:

Acremonium sp. Po-060 (FERM P-15862 deposited at the Japanese National Institute of Bioscience and Human Technology).

The rough bluegrasses into which an endophyte is introduced also include later generations of grasses.

The method by which the endophytic fungus, i.e. endophyte, is introduced into rough bluegrasses, will now be described. An endophyte living in plants occurring in nature is isolated and artificially cultivated, and the rough bluegrass is inoculated with the cultivated endophyte. The endophyte is then introduced into the rough bluegrass by infecting the grass with the inoculated endophyte.

In this inoculation step, conidiospores of the endophyte may suitably be used and the aforesaid endophyte deposited at the National Institute of Bioscience and Human Technology may be used to inoculate the grass.

The method of introducing an endophyte into bluegrasses according to another aspect of this invention will now be described in further detail as a sequence of stages.

Stage 1 Detection for presence or absence of endophyte, and isolation of same (1) Detection of endophyte infection A leaf with its sheath is removed from a plant collected in a search, the epidermis peeled, stained with aniline blue solution, and any endophyte in the tissue detected by examination with an optical microscope.

(2) Isolation and culture of endophyte

After sterilizing plant sections confirmed to contain endophyte, the endophyte is transplanted to an endophyte isolation culture and cultured for several months.

(3) Classification of endophyte

Isolated endophyte is classified according to the host, or grown under various environmental conditions using the flat plate culture method and classified according to its morphology. Alternatively, a liquid culture is performed and classified according to morphology, a slide culture performed and classified according to morphology.

Stage 2 Alkaloid analysis

Alkaloid produced either by the fungus alone or when living on the plant is analyzed and examined in particular for insect resistance. Analysis for disease resistance, environmental stress resistance and growth enhancement may be made at the same time.

Stage 3 Introduction of endophyte

The isolated endophyte is artificially introduced into the desired or target bluegrass. The endophyte may be introduced by directly inoculating the plant with it, alternatively non-differentiated cells such as callus can be inoculated with the endophyte and the plant regenerated from the callus. An appropriate method should be chosen according to the type of plant in which it is desired to introduce the endophyte.

Stage 4 Confirmation of presence of endophyte

An explant of a specimen into which endophyte has been introduced is stained with a dye solution, observed with an optical microscope, and the presence of endophyte or infection by it was detected by using the enzyme immunoassay method.

Stage 5 Examination of plants into which endophyte has been introduced (1) Insect resistance Using a plant into which endophyte had been introduced and a plant not containing endophyte, damage-causing pests were bred and a pest damage test was artificially conducted.

(2) Disease resistance

Using a bluegrass into which endophyte had been introduced and the same bluegrass not containing endophyte, an examination of resistance to disease-causing pathogenic fungi was made by inoculating the two types of plants and examining the extent of disease.

(3) Examination using later plant generations

Seeds containing endophyte were collected, germinated, and after confirming that the endophyte was present, the aforesaid tests were performed.

The above and other objects, features and advantages of the invention will be apparent from the following description of embodiments.

DETAILED DESCRIPTION OF THE PREFERRED EMBODIMENTS

EXAMPLE 1

(1) Detection of endophyte

Using the following method, endophyte was detected in plants of the genus Poa which are naturally occurring wild grasses.

The epidermis of leaves and leaf sheaths of these plants were removed, and the presence or absence of endophyte in the tissue was confirmed by examination with an optical microscope. This confirmation was performed as follows. 5 ml of lactic acid, 10 ml of glycerine, 5 ml of water and 0.02 g of an aqueous solution of aniline blue were placed on a glass slide. The leaf sheath was removed with forceps, and the underside epidermis was peeled away toward the leaf vein. The peeled epidermis was placed on the glass slide, covered with a cover glass, warmed in the flame of a gas burner and the tissue observed with an optical microscope. When the endophyte is present, the mycelium appears blue, so it is possible to detect the endophyte by this procedure.

As a result, endophyte was detected in one type of plant belonging to the genus Poa. From the life cycle of the fungus, it was found that this was an Acremonium endophyte with only asexual generation which did not move outside the plant.

(2) Isolation of endophyte

The endophyte was isolated through the following method from plants of the genus Poa wherein endophyte was detected by the aforesaid method (1).

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed 3 times with sterile water, transferred to an endophyte isolation culture, and cultivated in the dark at 25° C.

The isolation culture was prepared by sterilizing PDA (potato dextrose agar) culture adjusted to pH 5.6 at 121° C. for 15 minutes, adding penicillin and streptomycin so that their respective concentration were 100 mg/l, and pipetting 20 ml portions into plastic Petri dishes of diameter 9 cm.

After developing the culture for approx. 3–8 weeks, the mycelium was isolated from the explant, the colonies being removed by a cork borer of diameter 5 mm, transferred to the same PDA culture and grown.

(3) Classification and identification of endophyte by colonies using the flat plate culture method The mycelium transplanted to the PDA culture was grown in the dark at 25° C., and the colonies formed were examined. As a result, all the colonies on the culture were white and cottony. They grew relatively slowly, and in one month had reached a radius of only about 3 cm.

The endophyte which had been isolated was deposited at the National Institute of Bioscience and Human Technology, which is part of the Industrial Science and Technology Agency, its name and number being as follows:

Acremonium sp. Po-060 (FERM P-15862).

(4) State of mycelium by slide culture

A PDA culture of thickness 2–3 mm was mounted on a glass slide, the mycelium grew on the culture, and the characteristics of the mycelium and formation of conidiospores were examined. This cultivation was performed at 25° C. in the dark.

As a result, it was found that the mycelia were completely colorless, their width was 1–2 $\mu$m, and partitions were observed in all of them. All the mycelia were easily able to form conidiospores.

The conidiospores were formed at the ends of single phialides emerging from the ends or sides of the mycelium, and most of them were single conidiospores.

All the conidiospores were colorless, and were unicellular. Most of them were kidney-shaped and 3–8×1–3 $\mu$m in size. The phialides formed were all cylindrical tapering towards the ends, and separated from the mycelium by partitions.

(5) Analysis of plant alkaloids

An analysis of alkaloids from the host plants of Acremonium sp. Po-060 (FERM P-15862) was performed by the following method.

After freeze-drying the leaves and leaf sheaths of the plants, a 100 mg sample was placed in a mortar and crushed, 1.5 ml each of methanol and chloroform were added and blended, and the liquid recovered in a centrifuge sedimentation tube. The mixture was carefully blended at 18° C. for 30 minutes, 3 ml each of n-hexane and water were added and the mixture was stirred for 30 minutes. After centrifuging at 2000 r.p.m. for 10 minutes, an organic layer and an aqueous layer were separated.

3 ml of the aqueous layer was purified on a Biorad Ag2×8 and an Analytichem Blond Elut CBA column, and after concentration, 100 $\mu$l of 80% methanol was added. 20 ml samples were dripped onto thin layer plates coated with Merck silica gel 60 and using a chloroform, methanol, acetic acid and water mixture in the ratio 20:10:1:1 as developer, an analysis was performed by TLC (thin layer plate chromatography).

500 $\mu$l samples of the organic layer fraction were placed in 2 ml Eppendorf tubes, and after completely evaporating the solvent off in a vacuum evaporator centrifuge, the product was diluted to 200 ml with chloroform. After dilution, 3 ml of each sample was dripped onto a thin layer plate coated with Merck silica gel 60, and an analysis was performed by TLC using chloroform and methanol in the ratio 9:1 as developing solvent.

After developing, the water layer and organic layer extracts were confirmed by UV, and the color reaction and Rf values were measured by using the Ehrlich reagent (solution of 1.0 g p-dimethylbenzaldehyde in 96% ethanol) and nitrosonaphthol reagent.

For the Ehrlich reagent, the aqueous layer extract from the host plants gave a bluish purple spot. This color reaction and Rf value confirmed the presence of an indole alkaloid.

Also, the organic layer extract from the host plants using the Ehrlich reagent gave a bluish purple spot for all plants. For nitrosonaphthol reagent, a reddish purple spot was obtained at the same position. These color reactions confirmed the presence of indole alkaloids.

(6) Liquid growth culture

After growing Acremonium sp. Po-060 (FERM P-15862) for 2 months on a PDA culture at 25° C. in the dark, colonies were removed by a cork borer of diameter 5 mm, 100 ml of PD (potato dextrose) broth was placed in each of 300 ml flasks with shaking, one colony which had been sterilized at 121° C. for 15 minutes introduced in each flask, and shaking performed at 25° C. with a back and forth motion at 150 r.p.m.

As a result, for all colonies, the fungus spread through the whole flask in two weeks.

(7) Artificial inoculation using plants

Rough bluegrass was artificially inoculated using the isolated endophyte. The plant used here was a rough bluegrass of the Sabre strain. Herein, the Sabre used was that sold commercially by Takii Seed Co. Ltd.

The aforesaid endophyte was first grown according to the method of (2), transferred to a fresh PDA culture, and grown under the same conditions for 5–12 days. Inoculation was performed by sterilizing and germinating seeds on a WA (Water Agar) base culture obtained by adding 0.8% Agar to water, and cultivating the seedlings in the dark. 3–7 days after beginning culture, an incision was made in the plant with a knife, and mycelium which had been cultured on the PDA culture was dripped in.

After 8 days culture in the dark at 25° C. and 30° C., the plants were placed under illumination at 15° C. for 16 hours, cultured for 4 days, then grown under illumination at 25° C. for 16 hours, and cultured for at least 2 days. Plants which had turned green were transplanted and acclimatized.

By applying the method described in (1) to confirm the presence of endophyte, it was confirmed that the endophyte had been introduced into the plants. The infection rate was clearly higher at 30° C. than at 25° C.

(8) Artificial inoculation using callus

Callus was induced in rough bluegrass as a test sample for artificial inoculation. The Sabre strain of rough bluegrass was used to provide specimens. A callus induction culture was prepared by adding 2.0 mg/l of 2,4-D (2,4-dichlorophenoxyacetatic acid) and 0.2 mg/l of BAP (6-benzylaminopurine) to an MS base culture.

Seedlings obtained immediately after germinating on an MS culture were transplanted to callus induction cultures, and cultured for 2 months in the dark at 25° C. so as to obtain callus which had differentiating ability.

Artificial inoculation with Acremonium sp. Po-060 (FERM P-15862) was performed by using callus from rough bluegrass. A callus was first induced on the aforesaid induction culture, and the callus obtained was transferred to an MS base culture without the addition of plant hormone.

After transferring, the callus was immediately cut with a knife, and 50 µl of mycelium per callus, grown as in (6), was dripped in.

The callus was cultured for several weeks in the dark at 25° C. and 30° C., then placed under illumination for 16 hours, or alternatively it was placed under illumination for 16 hours from the start. The regenerated plant was then transferred to a fresh MS culture and grown for one month. When an examination was made for presence of endophyte according to the method described in (1), it was found that the endophyte had been introduced.

(9) Mass production of conidiospores

Conidiospores were mass produced by using Acremonium sp. Po-060 (FERM P-15862). This fungus was cultured by the same method as that of (6), and transferred to a fresh PD culture. 20 ml of culture liquid was removed after 5–12 days when the ability to form conidiospores is at a peak, and unwanted mycelium was removed by two superposed 20 µm meshes. 10 ml of the filtrate was placed in a centrifuge tube, and centrifugation was performed at 1000 r.p.m. for 10 minutes. After centrifuging, the supernatant liquid was discarded and 1 ml of PD culture was added so as to obtain a suspension of conidiospores.

(10) Inoculation method using conidiospores

The Sabre strain of rough bluegrass was artificially inoculated with a conidiospore suspension of Acremonium sp. Po-060 (FERM P-15862) using the callus inoculation method described in (8). After examining the plants obtained by the method described in (1), it was found that the endophyte had been introduced with high frequency, and there was a large significant difference compared to the inoculation method of (8) using the mycelium.

(11) Detection of endophyte by enzyme immunoassay method (ELISA)

The endophyte was detected from leaf sections of plants into which it had been introduced by the artificial inoculation methods of (7), (8) and (9) as follows.

Buffer solution was introduced into 0.5 g raw weight of the explant, and the mixture was crushed in a mortar so as to obtain an extract. 50 ml of this extract was placed in a well in a microplate, and adsorbed at room temperature for 30 minutes. Uncombined antigen was then washed out.

The well was filled with blocking solution (3% skimmed milk solution) and washed 30 minutes later. Anti-endophyte rabbit antiserum (primary antibody) was added to the well, reacted at room temperature for 60 minutes, and uncombined antibody was washed out.

Diluted secondary antibody (antirabbit IgG, goat labelled with alkali phosphatase) was added to the well, reacted at room temperature for 60 minutes, and uncombined antibody was washed out. A basic solution was then added to the well so as to cause an alkali phosphatase reaction. The reaction was stopped by 0.5N NaOH, and the degree of light absorption at 405 nm was measured.

As a result, all specimens into which endophyte had been introduced by the methods described in (7), (8) and (9) gave a color reaction, thus proving the presence of this endophyte in rough bluegrass.

(12) Resistance to webworm

Using rough bluegrass (Sabre strain) into which the endophyte Acremonium sp. Po-060 (FERM P-15862) had been introduced as described in (7) (referred to hereafter as Sabre E+), resistance to webworm was examined.

Sabre E+ was acclimatized for 2 months after inoculation. As a comparison, seeds of Sabre which had not been inoculated (referred to hereafter as Sabre E−) were immersed in 70% ethanol for 10 seconds, immersed in 2.5% aqueous sodium hypochlorite solution for 10 minutes, washed 3 times with sterile water, dried, transferred to an MS base culture, germinated and acclimatized after 2 months growth.

Sabre E+ and Sabre E− leaf sections were respectively cut into lengths of approximately 1 cm, and three of each were placed in a Petri dish of diameter of 9 cm. Immediately after hatching, approx. 200 webworm larvae were transferred to the dish, and damage to the leaf sections after 24 hours was examined. As a result, it was found that whereas Sabre E− had been damaged by the larvae, Sabre E+ was completely free of damage.

(13) Resistance to curvularia spot

Drechslera sp., Curvularia sp. and Bipolaris sp. isolated from curvularia spot occurring in rough bluegrass were respectively grown on a PDA culture for 2 weeks, then conidiospores which had formed on the surface of the colonies were removed with a needle, suspended in sterile water and their concentration adjusted to 5000–10000/ml.

Sabre E+ plants in their 2nd month after inoculation were used. As a control, seeds from Sabre E− which had not been inoculated were immersed in 70% ethanol for 10 seconds, immersed in 2.5% aqueous sodium hypochlorite solution for 10 minutes, washed 3 times with sterile water, dried in a current of air, transferred to an MS base culture, germinated and grown for 2 months. Ten of these specimens were placed in each of 6×6×10 cm plant boxes containing a sterile culture medium, and grown for 2 weeks.

To inoculate the plants with pathogenic fungi, the entire surfaces of the plants were sprayed or coated with the suspended solution of the pathogenic fungi, and the plants grew at 28° C. for one month under 16 hour daylight conditions.

As a result, for all pathogenic fungi, leaf rot started in from the tip of the leaf from the first week after inoculation in the control group, and by the third week all the leaves of the plants had withered and died. On the other hand in the case of Sabre E+ containing endophyte, although there were black spots in the initial stage of infection having a diameter of approx. 2 mm on the leaves, and curvularia spot was found up to approx. 1 cm from the tip of the leaf, there was effectively no further spreading of blotches. A significant difference was thus clearly observed with respect to curvularia spot caused by Drechslera sp., Curvularia sp. and Bipolaris sp.

(14) Resistance to rust

Summer spores formed on the leaves of rough bluegrass infected with black rust were made to adhere to a moist filter paper of size 5×5 mm. The filter paper carrying the summer spores was placed on the leaves of Sabre E+ prepared by the same method as described in (12) and of plants in a control group so as to inoculate the plants. The inoculated plants were incubated at 20° C. at high humidity in the dark for 12 hours, placed under illumination for 16 hours, and cultivated for 3 weeks.

As a result, 10 days after inoculation, clumps of summer spores were formed on the surfaces of the leaves of both Sabre E+ and the control group. However whereas in the control group the entire plant was covered with a secondary formation of many clumps of summer spores within 2 weeks, in Sabre E+ there were very few newly formed clumps and they did not cover the entire plant surface. Hence, there was clearly a significant difference in the occurrence of this disease.

EXAMPLE 2

(1) Resistance to lawn cutworm

Using rough bluegrass into which endophyte had been introduced by the method of (7) in Example 1, resistance to lawn cutworm was examined. This examination was performed by the same method as that of (12), i.e. using approx. 200 lawn cutworm larvae which had just hatched, the damage after 24 hours was examined.

As a result, it was found that whereas Sabre E− had been totally damaged by the larvae, only a small part of Sabre E+ had been damaged.

Next, the plants prepared by the method of (12) were placed in 20×30 cm pots, 10×10 cm turfs of Sabre E+ and Sabre E− were prepared, approximately 50 larvae which had hatched 2 weeks earlier were introduced, and the damage after 4 days was examined.

As a result, whereas Sabre E− was totally ravaged by the larvae, Sabre E+ still retained a large number of its green leaves.

The same type of turf was grown by vegetative propagation, 40×40 cm turfs of Sabre E+ and Sabre E− were planted outdoors, 7 larvae which had hatched at least 3 weeks earlier were released respectively on each block, and the resulting damage was examined.

As a result, damage progressively began to appear. However whereas Sabre E− was totally ravaged after 4 days, Sabre E+ still retained a large number of its green leaves.

(2) Insect resistance using later generations of endophyte-infected plants

Seeds of Sabre E+ which had been artificially inoculated with endophyte and seeds of Sabre E− of the control group were collected after the plants had come into ear. After germination, endophyte was detected by the method of (1) of Example 1, and insect resistance was examined by the method of (12) of Example 1. As a result, it was found that whereas leaf sections of germinated Sabre E+ plants were completely undamaged, Sabre E− was totally ravaged. This shows that the benefit obtained by the presence of endophyte is the same even when propagated to later generations of plants via seed.

Having described specific embodiments of this invention, it is to be understood that the invention is not limited to those precise embodiments, and that various changes and modifications may be made by one skilled in the art without departing from the scope or the spirit of the invention as described in the appended claims.

What is claimed:

1. A method for introducing an endophytic fungus into a bluegrass comprising:
    isolating a filamentous endophytic fungus from a plant and artificially growing it, and
    artificially inoculating one of *Poa trivialis* and *Poa compressa*, not containing a filamentas endophytic fungus, with said artificially grown endophytic fungus to infect the same.

2. The method for introducing an endophytic fungus as defined in claim 1, wherein said endophytic fungus is isolated from a plant of genus Poa which is naturally occurring wild grass.

3. The method for introducing an endophytic fungus as defined in claim 1, wherein a section of wild plant containing the endophytic fungus is placed on an isolation culture and cultured for isolation of the endophytic fungus from said wild plant.

4. The method for introducing an endophytic fungus as defined in claim 1, wherein the isolated endophytic fungus is directly inoculated into the one of *Poa trivialis* and *Poa compressa*.

5. The method for introducing an endophytic fungus as defined in claim 4, wherein said isolated endophytic fungus is dripped in an incision made in said one of *Poa trivialis* and *Poa compressa* with a knife.

6. The method for introducing an endophytic fungus as defined in claim 1, wherein said isolated endophytic fungus is introduced into a differentiated cell of one of *Poa trivialis* and *Poa compressa* to regenerate a cell with the isolated endophytic fungus.

7. The method for introducing an endophytic fungus as defined in claim 1, wherein said isolated endophytic fungus is introduced into a callus of one of *Poa trivialis* and *Poa compressa* to regenerate a callus with the isolated endophytic fungus.

8. The method for introducing an endophytic fungus as defined in claim 7, wherein the callus is cut, and mycelium of said isolated endophytic fungi is dripped in the callus.

9. The method for introducing an endophytic fungus as defined in claim 1, wherein conidiospores of said endophytic fungus are artificially inoculated.

10. The method for introducing an endophytic fungus as defined in claim 9, wherein each of said conidiospores is formed at an end of single phialides emersing from a mycelium.

11. The method for introducing an endophytic fungus as defined in claim 1, wherein said endophytic fungus is Acremonium sp. Po-060(FERM P-15862 deposited at the Japanese Institute of Bioscience and Human Technology).

12. The method for introducing an endophytic fungus as defined in claim 1, further comprising examining plants into which said endophytic fungus has been introduced for insect resistance.

13. The method for introducing an endophytic fungus as defined in claim 1, further comprising examining plants into which said endophytic fungus has been introduced for disease resistance.

14. The method for introducing an endophytic fungus as defined in claim 1, further comprising examining plants into which said endophytic fungus has been introduced for environmental stress resistance.

15. The method for introducing an endophytic fungus as defined in claim 1, further comprising examining plants into which said endophytic fungus has been introduced for growth enhancement.

* * * * *